US00PP31889P2

(12) United States Plant Patent
Hansen

(10) Patent No.: US PP31,889 P2
(45) Date of Patent: Jun. 16, 2020

(54) ***ECHINACEA* PLANT NAMED 'CORAL CRAZE'**

(50) Latin Name: ***Echinacea* hybrid**
Varietal Denomination: Coral Craze

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,943

(22) Filed: Feb. 1, 2019

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 6/1448
See application file for complete search history.

*Primary Examiner* — Anne Marie Grunberg

(57) ABSTRACT

The new and distinct cultivar of *Echinacea* plant named 'Coral Craze', with fragrant flowers on strong stems having coral pink ray florets that mature to lavender-pink with large orange center cone and near black stems; The flowers from mid-summer to late summer, and is suitable as a potted plant, for the landscape, and for cut flower arrangements.

1 Drawing Sheet

Botanical denomination: *Echinacea* hybrid.
Cultivar designation: 'Coral Craze'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Jun. 18, 2018 by Walters Gardens, Inc., who obtained the plant and all information relating thereto, from the inventor. No plants of *Echinacea* 'Coral Craze' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of Coneflower from the genus *Echinacea* and given the cultivar name 'Coral Craze'. The new plant was the result of a self-pollination by the inventor of an unnamed proprietary hybrid known as 12-2-1 on Jun. 23, 2014 at a wholesale perennial nursery in Zeeland, Mich. This seedling was evaluated first in trials in the summer of 2016 at the same nursery and assigned the breeder code of 14-4-2. *Echinacea* 'Coral Craze' has been asexually propagated at the same nursery by crown division since 2016 and also using careful shoot tip tissue culture procedures and found to reproduce plants that exhibit all the characteristics identical to the original plant.

*Echinacea* 'Coral Craze' is distinct from all other Coneflowers known to the inventor. The nearest comparison cultivars are 'Kim's Knee High' U.S. Plant Pat. No. 12,242, 'Red Knee High' U.S. Plant Pat. No. 20,411, 'Glowing Dream' U.S. Plant Pat. No. 24,329, 'Solar Flare' U.S. Plant Pat. No. 22,133, 'Little Annie' (not patented) and 'Delicious Candy' (not patented). The parent plant, 12-2-1, has more upright, denser flower stems with smaller foliage and smaller flower heads. 'Kim's Knee High' has lighter pink ray petals on slightly shorter stems, and the ray petals are smaller and droop more than the new plant when young. 'Red Knee High' is slightly shorter in habit and has rich magenta ray flowers that droop significantly more than the new plant. 'Glowing Dream' has ray flowers that are watermelon pink on slightly smaller plants. 'Solar Flare' produces wider flower heads and has ray flowers that are more magenta-orange on taller plants. 'Little Annie' is shorter in habit, the flower heads are smaller and the ray flowers are lighter magenta.

SUMMARY OF THE INVENTION

*Echinacea* 'Coral Craze' has not been evaluated under all possible environmental conditions. The phenotype may vary with variations in environment including: growing temperature, available sunlight, nutrients, water, etc. without a change in the genotype of the plant. The new plant is distinct from its parents and all other *Echinacea* known to the applicant in the following combined traits:

1. Fragrant flowers on strong near black stems.
2. Large, broad flower heads.
3. Ray petals of coral-pink mature to lavender-pink.
4. Vigorous growth and excellent habit.

BRIEF DESCRIPTION OF THE DRAWINGS

The photographs of the new invention demonstrate the overall appearance of the plant including the unique traits. The drawings of the new plant are of a two-year-old plant grown in full-sun trial garden in Zeeland, Mich. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
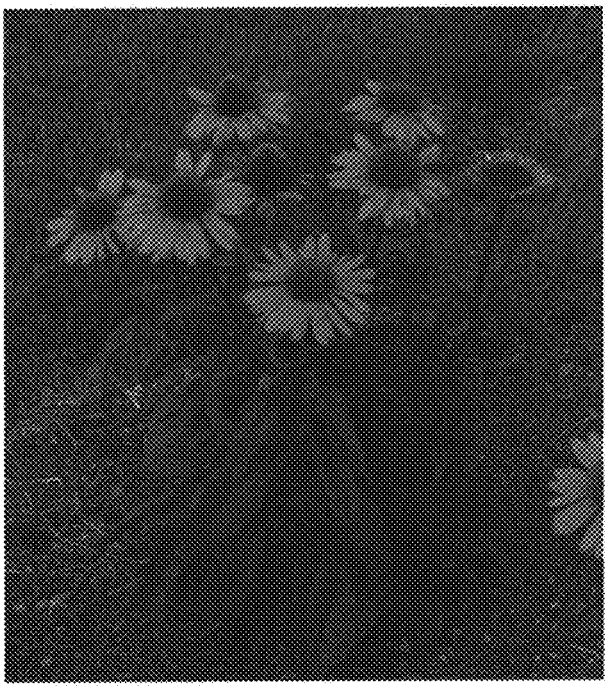
FIG. 1 shows the habit of the new plant in flower.
Figure 2:
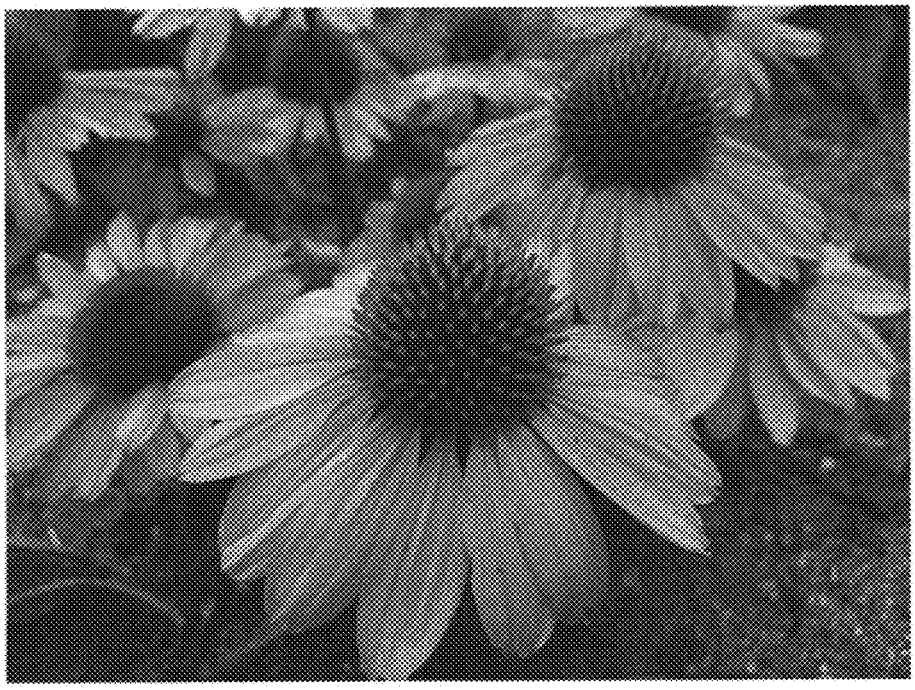
FIG. 2 shows a close up of a flower of the new plant.

The following description of *Echinacea* 'Coral Craze' is based on observations of two-year-old specimens grown in a full-sun trial garden with supplemental water and fertilizer in Zeeland, Mich. The new plant has not been tested in all environments and some phenotypic differences may occur with different environments without, however, any change in genotype. The color descriptions are based on the 2015 edition of The Royal Horticultural Society Colour Chart except where common dictionary descriptions are used.

Parentage: Female and male parent is the proprietary unreleased hybrid 12-2-1, which is a selection of a self-pollinated seedling from a cross of 'Little Annie' times 'Solar Flare';

Plant habit: Multi-stemmed, freely-branched, hardy herbaceous perennial, flowering to about 70 cm tall and 65 cm wide;

Growth rate: Vigorous, finishing in 4 liter containers in about 2 months during the summer;

Roots: Cream-colored, finely branched;

Foliage: Alternate; ovate; acute apex; attenuate base; margin entire; hirsutulous both surfaces; to about 22.5 cm long and 10.0 cm wide decreasing distally, average about 12.0 cm long and 5.0 cm wide;

Leaf color: Adaxial between RHS 136A and RHS 139A, abaxial nearest RHS 138A;

Venation: Pinnate; with two major arcuate veins on both sides of the midrib; abaxial midrib and veins costate;

Vein color: Abaxial midrib and secondary veins nearest RHS 145D, adaxial midrib and secondary veins between RHS 145D and RHS 138D;

Petiole: Hirtellous, concavo-convex, about 8.0 cm long and 2.5 mm wide on lowest leaves and decreasing to sessile distally; color nearest RHS 145D adaxial and abaxial;

Peduncle: Hirsutulous; cylindrical; average 18.0 cm long and 8.5 mm diameter; quantity per plant about ten;

Peduncle color: Nearest RHS 187A;

Pedicel: Hirsutulous, cylindrical; average 10.0 cm long and 6.0 mm diameter;

Pedicel color: Nearest RHS 187A;

Inflorescence: Bracteate head, aggregate of achene; with distinct ligulate ray florets and disk florets in a pappus; flowering mid-summer to late summer; initial flowers largest, to about 12.7 cm wide, average about 10.0 cm diameter with cones 4.5 cm across and 4.0 cm tall; approximately 8 flowers per peduncle; sweetly fragrant;

Flower persistence: Remaining affective in color for 10 to 14 days depending on temperatures, cone drying on plant and effective into winter;

Involucre: With numerous bracts, about 48 per flower; arcuate downward toward pedicle;

Involucre bracts: Lanceolate; narrowly acute apex; truncate base; entire margin; average about 12.0 mm long and 3.5 mm across; color nearest RHS 139A on adaxial and abaxial margin, nearest RHS 146B in adaxial and abaxial center;

Flower buds with ray florets vertical: About 20.0 mm across and 20.0 mm tall; ray floret color nearest RHS 186C with apices nearest RHS 147A, cone color nearest RHS 187A;

Ray florets: Petals arrangement in single whorl, frequently imbricate; lanceolate, apex emarginated, base attenuate; margin entire; 24 to 28 per flower; opening to horizontal, drooping up to only 15 degrees below horizontal; to 4.8 cm long and 12.0 mm wide, average size 3.8 cm long, 9.5 cm wide at center tapering to 2 mm wide at base; thickened midrib raised;

Disc florets: About 400 to 600 per head; in raised dome, about 4.5 cm across and 4.0 cm tall; outer florets about 8.0 mm long and 2.0 mm wide, central florets about 11.0 mm long and 2.0 mm wide; RHS 143C near base of corolla tube and RHS 167B near apex of petal;

Disk floret androecium:

Staminal column: About 1 mm wide and protrudes from corolla tube about 2 mm; five fused stamens; color nearest RHS 169C;

Filaments: Five; attached to column; thin, less than 0.2 mm diameter and 1.5 mm long; color nearest RHS 158D;

Pollen: Globose, less 0.1 mm in diameter, RHS 178A;

Fruit: Achene; about 4 mm long and 2 mm wide; between RHS 199A and RHS 199B;

Disease resistance: Resistance beyond that of other hardy Coneflower cultivars has not been observed. The plant grows best with plenty of moisture and adequate drainage, but is able to tolerate some drought when mature. Hardiness at least from USDA zone 4 through 8.

I claim:

1. A new and distinct cultivar of *Echinacea* plant named 'Coral Craze' as herein described and illustrated.

* * * * *